United States Patent
Kim et al.

(10) Patent No.: US 7,572,831 B2
(45) Date of Patent: Aug. 11, 2009

(54) COMPOSITION CONTAINING CHALCONE

(75) Inventors: Min-Young Kim, Daejeon (KR);
Byung-Young Park, Daejeon (KR);
Kyoung-Mi Kim, Cheonju (KR);
Nack-Do Sung, Daejeon (KR);
Pyung-Keun Myung, Daejeon (KR)

(73) Assignee: Angiolab, Inc., Daejeon (KR)

( * ) Notice: Subject to any disclaimer, the term of this patent is extended or adjusted under 35 U.S.C. 154(b) by 550 days.

(21) Appl. No.: 10/838,853

(22) Filed: May 3, 2004

(65) Prior Publication Data

US 2004/0209952 A1 Oct. 21, 2004

Related U.S. Application Data

(63) Continuation-in-part of application No. PCT/KR02/02031, filed on Oct. 31, 2002.

(51) Int. Cl.
*A61K 31/235* (2006.01)
*A61K 31/12* (2006.01)

(52) U.S. Cl. .................... 514/545; 514/689

(58) Field of Classification Search ............... 514/545, 514/689
See application file for complete search history.

(56) References Cited

U.S. PATENT DOCUMENTS

| | | | | |
|---|---|---|---|---|
| 6,051,602 A * | 4/2000 | Bissett | ........... | 514/456 |
| 6,093,411 A * | 7/2000 | Bissett | ........... | 424/401 |
| 6,183,761 B1 * | 2/2001 | Bissett et al. | ........... | 424/401 |
| 6,235,773 B1 * | 5/2001 | Bissett | ........... | 514/456 |
| 6,444,647 B1 * | 9/2002 | Robinson et al. | ........... | 514/17 |
| 6,462,075 B1 * | 10/2002 | Bowen et al. | ........... | 514/460 |
| 6,492,326 B1 * | 12/2002 | Robinson et al. | ........... | 514/2 |
| 7,235,249 B2 * | 6/2007 | Bissett | ........... | 424/401 |

FOREIGN PATENT DOCUMENTS

| | | |
|---|---|---|
| EP | 0998939 A | 5/2000 |
| WO | WO 9912904 A | 3/1999 |
| WO | WO 9900114 A | 8/1999 |
| WO | WO 9947119 A1 * | 9/1999 |
| WO | WO 0146110 A | 6/2001 |

OTHER PUBLICATIONS

Nakajima et al., Cancer Research, vol. 49, pp. 1698-1706, Apr. 1, 1989.*
Baker et al., Journal of Cell Science, vol. 115(19), pp. 3719-3727, 2006.*
Catterall et al., Arthritis Research and Therapy, vol. 5, No. 1, pp. 12-24, 2003.*
Greenwald, R.A., Annals New York Academy of Sciences, 878:413-419, 1999.*
"Vascular Cell adhesion Moledule 1 (VCAM-1) Activation of Endothelial Cell Matrix Metalloproteinases:Role of Reactive Oxygen Species", Deem et al., Blood, 2004, vol. 104, No. 8, pp. 2385-2393.*
Filsiak et al., JEADV, 2005, 19, pp. 418-421.*
Blood, 2004, vol. 104, No. 8, pp. 2385-2393.*

* cited by examiner

*Primary Examiner*—Brian-Yong S Kwon
(74) *Attorney, Agent, or Firm*—Joseph Hyosuk Kim; JHK Law

(57) ABSTRACT

The present invention provides an MMP-inhibitory composition comprising chalcone or its derivatives. They inhibit the MMPs in collagenase subfamily as well as those in gelatinase subfamily. The MMP inhibitory activity of chalcone derivatives was similar to or greater than that of parent compound, chalcone. Chalcone or its derivatives of the present invention inhibit activity of matrix metalloproteinase, so that it can be applied to treat and prevent diseases related to matrix metalloproteinase.

13 Claims, 7 Drawing Sheets

COMPOSITION CONTAINING CHALCONE

CROSS-REFERENCE TO RELATED APPLICATIONS

The present application is a continuation-in-part application claiming benefit of priority to PCT/KR02/02031, filed on Oct. 31, 2002, the contents of which are incorporated by reference herein in its entirety.

BACKGROUND OF THE INVENTION

1. Field of the Invention

The present invention relates to a pharmaceutical composition comprising chalcone or its derivatives having matrix metalloproteinase inhibitory activity.

2. General Background and State of the Art

Chalcones (or chalcone derivatives) are compounds having the basic C6-C3-C6 arrangement in which middle three carbon atoms do not form a closed ring. These are important precursors in the synthesis of pigment in plant. Since they have anti-oxidant effect, they can do protective action from the harmful UV irradiation (Woo W. S.; *Methodology of natural product chemistry* (Seoul National University Publishing), pp131-137). These compounds are abundant in the plant of the genus *Corepsis*. Chalcones in natural origin including 2'6'-dihydroxy-4-methoxychalcone, carthamin, and butein are identified from plants such as cinnamon, red pepper and carthamus flower. Dihydrochalcone is contained in certain species of the genus *Rosaceae* and *Rhododendron*, and phloridzin is one of the components in apple tree foliage (Hunter, M. D.; *Phytochemistry* (Oxford) 34, pp1251-1254, 1993). Chalcones are known as inhibitors for glucose transport and growth of various cells including cancer, which enables to apply them in the prevention from aging and/or cancer (Fuhrmann, G. F., Dernedde, S. and Frenking G.; *Biochimica Biophysica Acta*, 1110, pp105-111, 1992; Kobor, M., et al.; *Cancer Lett.*, 119, pp207-212, 1997; Calliste, C. A., et al.; *Anticancer Res.*, 21, pp3949-3956, 2001).

Matrix metalloproteinases (MMPs), a family of over 20 proteins are endopeptidase, which degrade or proteolyze the components of the extracellular matrix such as collagen, proteoglycan, and gelatin. They are classified into four groups: collagenase, gelatinase, stromelysin, and membrane-type MMP.

Collagenase proteolyzes the triple helix interstitial collagen and gelatin, and it comprises interstitial collagenase (MMP-1), neutrophil collagenase (MMP-8) and collagenase-3 (MMP-13). These three enzymes share more than 50% sequence similarity, having two zinc-binding sites and one or two calcium binding sites in their core domain (Borkakoti et al.; *Nature Struct. Biol*, 1, pp106-110, 1994; Bode, et al.; *EMBO J.*, 13, pp1263-1269, 1994; Lovejoy et al.; *Science*, 263, pp375-377, 1994).

Gelatinase can degrade denatured collagen and type IV, V, VII and X collagen. There are two gelatinases, one is 72 kDa gelatinase-A (MMP-2) secreted from fibroblast, and the other is 92 kDa gelatinase B (MMP-9) secreted from mononuclear phagocytes. They specifically act on type IV collagen, the major component of the basement membrane (Murphy, G. et al.; *Biochem. J.*, 258, pp463-472, 1989; Stetler-Stevenson, W. G. et al.; *J. Biol. Chem.*, 264, pp1353-1356, 1989). These enzymes are very important in cancer invasion and metastasis. As compared with MMP-2, MMP-9 comprises additional sequences with unknown functions between the C-terminal and catalytic domain (Wilhelm, S. M. et al.; *J. Biol. Chem.*, 264, pp17213-17221, 1989).

Stromelysins show a broad substrate spectrum and stromelysin-1 (MMP-3), stromelysin-2 (MMP-10), stromelysin-3 (MMP-11), and matrilysin (MMP-7) are classified as stromelysins (Chin, J. R. et al.; *J. Biol. Chem.*, 260, pp12367-12376, 1985; Whitham, S. E. et al.; *Biochem. J.*, 240, pp913-916, 1986).

Metalloelastinase (MMP-12) and membrane-type MMP such as MT1-MMP (MMP-14), MT2-MMP (MMP-15) and MT3-MMP (MMP-16), are also identified as enzymes in the MMP family.

Many enzymes in the MMP family have substrate specificity. The expression of MMP is induced under various physiological circumstances when remodeling of an extracellular matrix is required (Curry, T. E. Jr., Osteen, K. G.; *Biol. Reprod.*, 64, pp1285-1296, 2001; Damjanovske, S., et al.; *Ann. NY Acad. Sci.*, 926, pp180-191, 2000; Ravanti L, Kahari V M; *Int. J. Mol Med.*, 6, pp391-407, 2000).

Increased expression or activation of MMPs is observed in many pathological states, such as atherosclerosis, restenosis, MMP-dependent-osteopathy, inflammation of the central nervous system, Alzheimer's disease, asthma, skin aging, rheumatoid arthritis, osteoarthritis, septic arthritis, osteoporosis, endometriosis, corneal ulcer synechia, bone disease, proteinuria, abdominal aortic aneurysm, regressive cartilage loss, multiple sclerosis, myelinated nerve loss, liver fibrosis, nephroglomerular disease, germinal membrane ruptures, inflammatory bowel disease, gingivitis, periodontal disease, senile macular degeneration, diabetic retinopathy, proliferate vitreous body retinopathy, immature retinopathy, eye inflammation, corneal ulceration, Sjogren's syndrome, myopia, eyes tumors, rejection of cornea implantation, angiogenesis and cancer metastasis. (Woessner Jr.; *Ann. NY Acad. Sci.*, 732, pp11-21, 1994; Warner et al.; *Am. J. Pathol*, 158, pp2139-44, 2001; Stetler-Stevenson; *Surg. Oncol. Clin. N. Am.*, 10, pp383-92, 2001).

For example, stromelysins are known to be the major enzyme for disruption of cartilage (Murphy, G. et al.; *Biochem. J.*, 248, pp265-268, 1987). Collagenases, gelatinases and stromelysins are responsible for the degradation of the extracellular matrix in many retinopathies (Bruns, F. R. et al.; *Invest. Opthalmol. and Visual Sci.*, 32, pp1569-1575, 1989). Collagenases and stromelysins are identified in fibroblast from gingiva in inflammation and the activity of the enzyme is dependent on the degree of inflammation (Overall, C. M. et al.; *J. Periodontal Res.*, 22, pp81-88, 1987). MMP activity is highly enhanced in response to the bacterial infection and inflammation in gingival crevicular fluid taken from patients with periodontal disease. Destruction of collagen in the periodontal matrix by MMP leads to gingival recession, pocket formation and tooth movement (Goulb, L B., Ryan M. E. Williams R. C.; *Dent. Today*, 17, pp102-109).

Recent reports have also shown that MMP-1 activity is highly induced in Alzheimer's disease, and MMP-1 and MMP-3 are involved in the pathophysiology of the disease (Leake A, et al.; *J. Neurosci. Lett.*, 291 pp201-3, 2000; Yoshiyama Y, et al.; *Acta Neuropathol.* (Berl), 99, pp91-5, 2000).

It is also found that MMP-9 is the major MMP in bronchoalveolar lavage fluid and bronchial mucosa in asthma and MMP-2 and MMP-9 are crucial for the induction of bronchial asthma (Mautina et al., *J. Allergy Cli.n Immunol.*, 104, pp530-533, 1999; Kumagai et al., *J. Immunol.*, 162, pp4212-4219, 1999; Bechy Kelly et al., *Am J Respir Crit Care Med*, 162, pp1157-1161, 2000).

MMPs are also responsible in solar UV radiation-induced skin damage, affecting skin tone and resiliency leading to premature aging. The symptoms of which include leathery texture, wrinkles, mottled pigmentation and laxity. Therefore, MMP inhibitors could be included in cosmetics for anti-photoaging or anti-wrinkle treatment (Hase T et al.; *Br. J. Dermatol*, 142, pp267-273, 2000; Fisher G J; *Photochem. Photobiol.*, 69, pp154-157, 1999).

Since MMP inhibitors can be applied to the treatment and prevention of many diseases, development of MMP inhibitors as new therapeutics is expected. These inhibitors need to be administered for a long time, so that desirable inhibitors should not have toxic or adverse effect with good patient compliance.

SUMMARY OF THE INVENTION

As previously mentioned, chalcone or its derivatives of the present invention inhibits matrix metalloproteinase activity. Based on this, chalcone and its derivatives can be used as a new drug for treatment and prevention of MMP-dependent diseases.

Accordingly, it is an object of the present invention to provide a pharmaceutical composition comprising chalcone or its derivatives having matrix metalloproteinase (MMP) inhibitory activity.

The present invention is directed to a pharmaceutical or cosmetic composition comprising chalcone or its derivatives and salts thereof.

Chalcone or its derivatives according to the present invention are shown in formula (I);

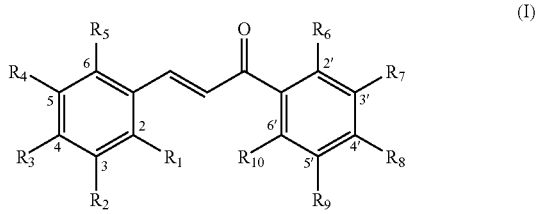

(I)

wherein
$R_1$ to $R_{10}$ are independently selected from H, OH group, a $C_1$-$C_3$ alkyl group, a halogen, an $OR_{11}$ group, COOH, $COOR_{12}$, an alkylene ester group according to the structure-$(CH_2)_m COOR_{12}$, or a $CF_3$ group;
$R_{11}$ is a C1-C4 alkyl group (preferably, C1-C3 alkyl), a benzyl of phenyl group or a $COR_{12}$ group;
$R_{12}$ is a C1-C20 alkyl group, preferably a C1-C3 alkyl group.

In accordance with an aspect of the present invention, there is also provided, preferably, an inventive chalcone derivatives such as phloretin, phloridzin, dihydrochalcone, 2',6'-dihydro-4'-methoxychalcone, 2-hydroxychalcone, 4-hydroxychalcone, 4'-hydroxychalcone, 4-methoxychalcone, 4'-methoxychalcone, 2',4'-dimethoxychalcone, carthamine, butein and its mixture, most preferably, 2-hydroxychalcone, 4-hydroxychalcone, 4-methoxychalcone, 4'-methoxychalcone and 2',4'-dimethoxychalcone.

In accordance with an aspect of the present invention, there is also provided a pharmaceutical composition to inhibit the activity of MMP such as MMP-1, MMP-2, MMP-9 and MMP-13.

It is an another object of the present invention to provide a pharmaceutical composition comprising chalcone or its derivatives for prevention and treatment of MMP-dependent diseases such as atherosclerosis, restenosis, MMP-dependent osteopathy, inflammation of central nervous system, Alzheimer's disease, asthma, skin aging, rheumatoid arthritis, osteoarthritis, septic arthritis, osteoporosis, endometriosis, corneal ulcer synechia, bone disease, proteinuria, abdominal aortic aneurysm, regressive cartilage loss, multiple sclerosis, myelinated nerve loss, liver fibrosis, nephroglomerular disease, germinal membrane rupture, inflammatory bowel disease, gingivitis, periodontal disease, senile macular degeneration, diabetic retinopathy, proliferate vitreous body retinopathy, immature retinopathy, eye inflammation, corneal ulceration, Sjogren's syndrome, myopia eye tumor, rejection of cornea implantation, angiogenesis, infiltration and cancer metastasis.

It is still another object of the present invention to provide a use of chalcone or its derivatives for the preparation of a pharmaceutical composition to treat MMP-dependent diseases.

It is still another object of the present invention to provide a method of treating MMP-dependent diseases such as atherosclerosis, restenosis, MMP-dependent osteopathy, inflammation of central nervous system, Alzheimer's disease, asthma, skin aging, rheumatoid arthritis, osteoarthritis, septic arthritis, osteoporosis, endometriosis, corneal ulcer synechia, bone disease, proteinuria, abdominal aortic aneurysm, regressive cartilage loss, multiple sclerosis, myelinated nerve loss, liver fibrosis, nephroglomerular disease, germinal membrane rupture, inflammatory bowel disease, gingivitis, periodontal disease, senile macular degeneration, diabetic retinopathy, proliferate vitreous body retinopathy, immature retinopathy, eye inflammation, corneal ulceration, Sjogren's syndrome, myopia eye tumor, rejection of cornea implantation, angiogenesis, infiltration and cancer metastasis with an effective amount of pharmaceutical composition according to the present invention.

These and other objects of the invention will be more fully understood from the following description of the invention, the referenced drawings attached hereto and the claims appended hereto.

BRIEF DESCRIPTION OF THE DRAWINGS

The present invention will become more fully understood from the detailed description given herein below, and the accompanying drawings which are given by way of illustration only, and thus are not limitative of the present invention, and wherein.

DETAILED DESCRIPTION OF THE PREFERRED EMBODIMENTS

Figure 1:
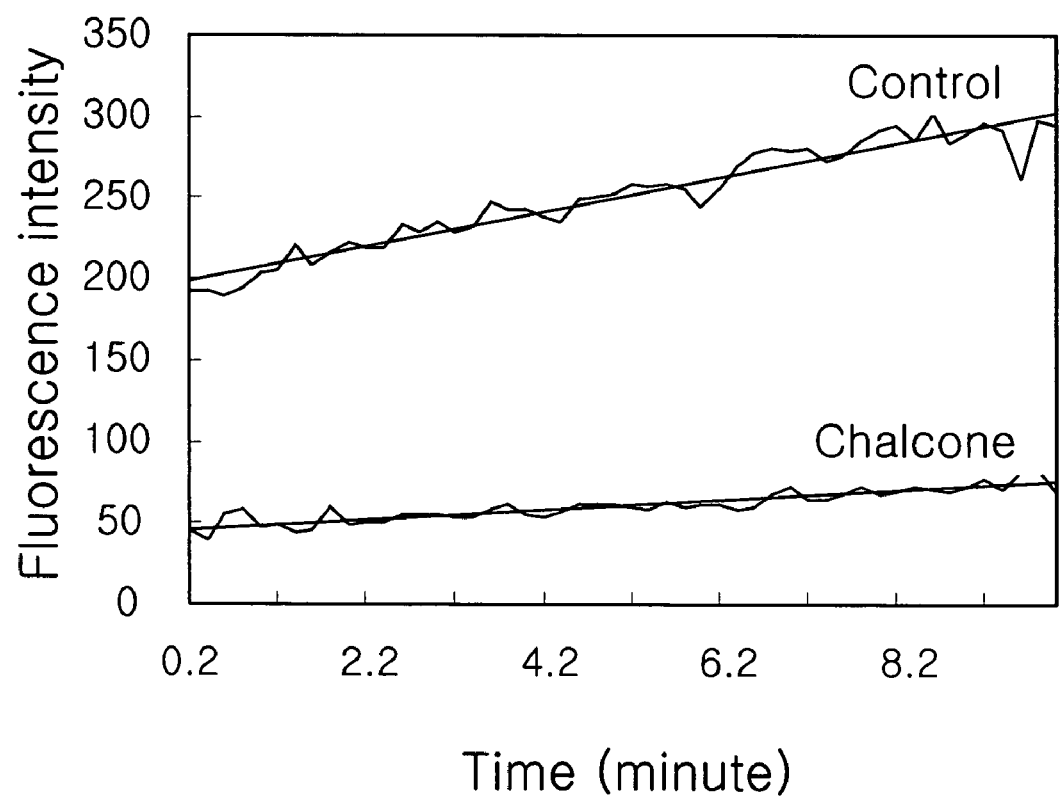
FIG. 1 is a graph showing the inhibition of MMP-1 by chalcone.

In the present application, "a" and "an" are used to refer to both single and a plurality of objects.

The inventors have recognized the inhibitory effect of chalcone or its derivatives on matrix metalloproteinase activity.

Therefore, the present invention provides a chalcone or its derivatives for prevention and treatment of MMP-dependent diseases.

Chalcone or its derivatives of the present invention can be purchased or synthesized with conventional methods.

An inventive chalcone or its derivatives may be prepared in accordance with the following preferred embodiment.

Benzaldehyde, substituted benzaldehyde, acetophenone or substituted acetophenone and sodium hydroxide are suspended in organic solvent and stirred at a temperature ranging from −20 to 50° C., preferably from 10 to 30° C., for a period ranging from 1 to 24 hours, preferably 3 to 10 hours. And then the mixture is neutralized with acid such as hydrochloric acid and extracted with ethylacetate. The extracted organic phase is removed under vacuum, followed by purification with silica gel column chromatography (eluant: n-hexane and ethylacetate mixture).

Above substituted benzaldehydes is selected from the group consisting of 2-hydroxybenzaldehyde, 4-hydroxybenzaldehyde and the like, and substituted acetophenone is selected from the group consisting of 4-methoxyacetophenone, 2,4-dimethoxyacetophenone and the like. Organic solvent is selected from the group consisting of methanol, ethanol, ethylacetate, acetone, ether and the like.

When the effect of chalcone or its derivatives on MMPs was investigated with MMP-1, MMP-2, MMP-9 and MMP-13, it drastically inhibited activity of all four enzymes. The inhibitory effect of chalcone and its derivatives on MMPs is not, however, limited to these enzymes.

In accordance with an aspect of the present invention, there is also provided a anti-angiogenic composition comprising chalcone or its derivatives of the present invention for inhibiting MMP activity In accordance with another aspect of the present invention, there is also provided a pharmaceutical composition comprising chalcone or its derivatives of the present invention as an active ingredient for prevention and treatment of MMP-dependent diseases.

The pharmaceutical composition of this invention may be used with more than one other composition. Preparation comprising chalcone or its derivatives can contain about 0.1-80 w/w %, preferably 1-30 w/w % chalcone or its derivatives as active ingredients. Topical formulation of the chalcone or its derivatives includes cream, lotion, ointment, aerosol, spray and paste. Desirable composition of the chalcone or its derivatives in the topical formulation is 0.001-60%, preferably 0.05-30%.

Accordingly, the present invention also provides a pharmaceutical composition for prevention and treatment of MMP-dependent diseases, which comprises chalcone or its derivatives as an active ingredient, in combination with pharmaceutically acceptable excipients, carriers or diluents. Pharmaceutical composition can be comprised in pharmaceutically acceptable diluent such as saline, buffered saline, dextrose, water, glycerol, ethanol and the mixture thereof, but it is not limited. Appropriate diluents are listed in the written text of Remington's Pharmaceutical Science (Mack Publishing co, Easton Pa.).

A pharmaceutical formulation may be prepared by using the composition in accordance with any of the conventional procedures. In preparing the formulation, the active ingredient is preferably admixed or diluted with a carrier or enclosed within a carrier, which may be in the form of a capsule, sachet or other container. When the carrier serves as a diluent, it may be a solid, semi-solid or liquid material acting as a vehicle, excipient or medium for the active ingredient.

Examples of suitable carriers, excipients, and diluents are lactose, dextrose, sucrose, mannitol, starches, gum acacia, alginates, gelatin, calcium phosphate, calcium silicate, cellulose, methylcellulose, microcrystalline cellulose, polyvinylpyrrolidone, water, methylhydroxybenzoates, propylhydroxybenzoates, talc, magnesium stearate and mineral oil. The formulations may additionally include fillers, anti-agglutinating agents, lubricating agents, wetting agents, flavoring agents, emulsifiers, preservatives and the like. The compositions of the invention may be formulated so as to provide quick, sustained or delayed release of the active ingredient after their administration to a patient by employing any of the procedures well known in the art.

Pharmaceutical formulations containing chalcone or its derivatives may be prepared in any form, such as oral dosage form (tablet, capsule, soft capsule, aqueous medicine, syrup, elixirs pill, powder, sachet, granule), or topical preparation (cream, ointment, lotion, gel, balm, patch, paste, spray solution, aerosol and the like), or injectable preparation (solution, suspension, emulsion). Topical formulations may be used for cosmetics purposes as well.

The pharmaceutical formulations comprising chalcone or its derivatives of the present invention can be administered via various routes including oral, transdermal, subcutaneous, intravenous, intraperitoneal, intramuscular, intra-arterial, rectal, nasal, ocular, and topical introduction. A daily dose of a chalcone or its derivatives is preferable from about 0.1 mg to 3 g, most preferably 1 to 1000 mg. In general, 5 to 2000 mg of chalcone or its derivatives can be administrated in a single dose or 2-3 divided doses per day.

Inventive pharmaceutical composition may be applied differently according to the purpose of dosing and diseases. It should be understood that the amount of active ingredient has to be determined with various factors. These factors include the severity of the patient's symptoms, other co-administrated drugs (e.g., chemotherapeutic agents), age, sex, body weight of the individual patient, food, dosing time, the chosen route of administration, and the ratio of the composition.

Regarding application of the chalcone to skin disorders, acne is a common skin disorder that characteristically presents with a skin eruption known as a comedone. There are two types of comedones, open and closed. An open comedone is commonly referred to as a blackhead. A closed comedone may appear reddish and inflamed and contain a papule full of pus. These closed comedones are commonly referred to as whiteheads.

The cause of acne is complex. A series of interrelated factors can determined how severe the disease will be. These factors include hormones, a proliferation of skin proteins called hyperkeratinization, a oily secretion called sebum, and bacteria. Data is presented regarding treatment of such skin disorders infra.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

EXAMPLES

Example 1

Synthesis of 4-methoxychalcone
(1-phenyl-3-(4-methoxyphenyl)prophenone)

Acetophenone (0.5 g) and sodium hydroxide (0.17 g) were suspended in 15 Ml of methanol pre-chilled at −10° C. p-Anisaldehyde (0.57 g) was added thereto, and stirred for 10 hr at room temperature. After neutralization with 5% hydrochloric acid solution, the product was extracted with 100 Ml of ethylacetate. The extracted organic phase was dried with anhydrous magnesium sulfate, and concentrated under vacuum evaporator. Purified compound was obtained by elution with n-hexane:ethylacetate (v/v, 1:7) through silica gel column chromatography (5×3 cm, Merk), and identified as follows:

m.p.=68~70° C.,
$^1$H-NMR (CDCl$_3$/TMS)d(ppm): 3.85(s, 3H), 6.9~7.0(d, 2H), 7.4~7.6(m, 6H), 7.7~7.8(d, 1H), 7.9~8.0(m, 2H)

Example 2

Synthesis of 2-hydroxychalcone
(1-phenyl-3-(2-hydroxyphenyl)prophenone)

2-Hydroxybenzaldehyde (2 g) and sodium hydroxide (0.72 g) were dissolved in 30 Ml of anhydrous toluene and refluxed for 3 hrs. The resulting salt was filtered with glass filter and completely dried. The preformed salt (2 g) and methoxymethyl chloride (1.29 g) were suspended in 30 Ml of anhydrous toluene and then stirred for 5 hrs. The product extracted with 100 Ml of ethylacetate was dried with anhydrous magnesium sulfate, and concentrated under vacuum evaporator. The product was 2.5 g of colorless liquid phase of 2-methoxymethyl-oxybenzaldehyde.

The previous product was mixed with acetophenone (2 g) suspended in methanol at −10° C. and stirred for 5 hr at room temperature. After neutralization with 5% hydrochloric acid solution, the product was extracted with 200 Ml of ethylacetate. The extracted organic phase was dried with anhydrous magnesium sulfate, and resulting 1-phenyl-3-(2-methoxymethyloxyphenyl)-prophenone was hydrolyzed with dilute alkaline solution. The reaction mixture was extracted with 200 Ml of ethylacetate. Extracted organic phase is dried with anhydrous magnesium sulfate and evaporated under vacuum. About 0.9 g of white solid (1-phenyl-3-(2-hydroxyphenyl) prophenone was obtained and subjected to silica gel column chromatography (5×3 cm, Merk). After being eluted with n-hexane:ethylacetate (v/v, 1:7), 0.7 g of purified compound was recovered and identified as follows:

m.p.=148~149° C.,
$^1$H-NMR (CDCl$_3$/TMS)d(ppm): 6.6~6.8(m, 2H), 6.9~7.05(t, 1H), 7.2~7.4(m, 5H), 7.4~7.6(d, 1H), 7.7~7.8(m, 2H), 9.4(s, 1H); Mass (m/z, relative intensity): 225(5, M+), 77(100)

Example 3

Synthesis of 4-hydroxychalcone
(1-phenyl-3-(4-hydroxyphenyl)prophenone)

This compound was prepared with 4-hydroxybenzaldehyde followed by same procedure as previously mentioned in Example 2. The purified compound (0.7 g) was identified as follows:

m.p.=182~183° C.,
$^1$H-NMR (CDCl$_3$/TMS)d(ppm): 3.5(s, 1H), 6.9(d, 2H), 7.5~7.7(m, 5H), 7.7~7.8(d, 1H), 8.0~8.1(m, 2H); Mass (m/z), relative intensity): 225(55, M+), 77(100)

Example 4

Synthesis of 4'-methoxychalcone
(1-(4-methoxyphenyl)-3-phenylprophenone)

4-Methoxyacetophenone (1.4 g) and sodium hydroxide (0.2 g) were suspended in 15 Ml of methanol pre-chilled at −10° C. The solution was kept for 1 hr under 0° C. with stirring. Benzaldehyde (1 g) was added thereto, and refluxed for 10 hr at room temperature with stirring. After neutralization with 5% hydrochloric acid solution, the product was extracted with 100 Ml of ethylacetate. The extracted organic phase was dried with anhydrous magnesium sulfate, and evaporated under vacuum. The resulting 1.3 g of white powder was purified through silica gel column chromatography (5×3 cm, Merk), which is eluted with n-hexane:ethylacetate (v/v, 1:7). The purified compound was identified as follows:

m.p.=98~100° C.,
$^1$H-NMR (CDCl$_3$/TMS)d(ppm): 3.85~3.9(s, 3H), 6.95~7.05(d, 2H), 7.4~7.45(m, 3H), 7.5~7.6(d, 1H), 7.6~7.7 (m, 2H), 7.75~7.85(d, 1H), 8.0~8.1(m, 2H); Mass (m/z, relative intensity): 239(14, M+), 77(100)

Example 5

Synthesis of 2',4'-dimethoxychalcone (1-(2,4-dimethoxyphenyl)-3-phenylprophenone)

It was prepared with 2,4-dimethoxybenzaldehyde followed by same procedure as previously mentioned in Example 4. The purified compound was identified as follows:
$^1$H-NMR (CDCl$_3$/TMS)d(ppm): 3.8~3.95(m, 6H), 6.45~6.6(m, 2H), 7.3~7.4(m, 4H), 7.5~7.65(m, 3H), 7.7~7.8 (m, 2H); Mass (m/z, relative intensity): 269(9, M+), 165(100)

Experimental Example 1

Effect of Chalcone Derivatives on Matrix Metalloproteinase Activity (1) Preparation of MMP MMP-1, MMP-2, MMP-9 and MMP-13 were cloned and prepared from insect cells (Sf21 insect cell) by using a Baculovirus system.

Each cDNA for corresponding MMPs was cloned to a pBlueBac4.5 transfer vector (Invitrogen, Cat no. V1995-20), and then transfected to Sf21 cells with a Bac-N-Blue Transfection Kit (Invitrogen, Cat no. K855-01). Sf21 cells were incubated with a TNM-FH (Sigma, St. Louis, Mo., U.S.A) media containing 10% fetal bovine serum at 27° C., then harvested and re-suspended at a concentration of $10^7$ cell/Ml. The cell suspension was incubated with a virus containing the cloned gene for 1 hr at room temperature. Infected Sf21 cells were grown for 72 hrs and the medium was recovered, and the MMP was purified. MMP-2 (GENEBANK No. XM_048244) and MMP-9 (GENEBANK No. XM_009491) were recovered from a gelatin-sepharose affinity column (Sigma, G5384) by eluting with 5% DMSO-containing buffer. MMP-1 (GENEBANK NO. XM_040735) and MMP-13 (GENEBANK NO. NM_002427) were purified with SP-sepharose column (Pharmacia, 17-02729-01) chromatography.

(2) Inhibition of MMP Activity

In order to investigate MMP inhibition by chalcone or its derivatives, MMP enzyme activity was assayed by a spectrofluorometric method using Perkin-Elmer LS50B.

Purified MMP-1, MMP-2, MMP-9 and MMP-13 were used after activation with 1 mM APMA before assay.

The substrate for MMP-1 was 2,4-dinitrophenyl-Pro-Leu-Ala-Leu-Trp-Ala-Arg-OH (Calbiochem). 2,4-dinitrophenyl-Pro-Leu-Met-Trp-Ser-Arg-OH (Calbiochem) was used for MMP-2 and MMP-9 activity assay. As a substrate for MMP-13, MCA-Pro-Cha-Gly-Nva-His-Ala-Dpa-$NH_2$ (Calbiochem) was used [MCA=methyl coumarylamide; Cha=L-cyclohexylalanine; Nva=L-norvaline; Dpa=3-(2,4-dinitrophenyl)-L-2,3-diaminoproprionic acid].

As a control, 2 Ml of reaction buffer (50 mM Tricine, pH 7.5, 10 mM $CaCl_2$, 200 mM NaCl) comprising DMSO, 10 nM of enzyme and 10 µM of substrate was prepared in a cuvette. Fluorescence intensity was measured for 5-10 min at room temperature with a spectrofluorometer.

50 µM Chalcone or its derivatives were added to a reaction buffer containing a substrate and enzyme, and fluorescence intensity was measured in the same manner.

Figure 2:
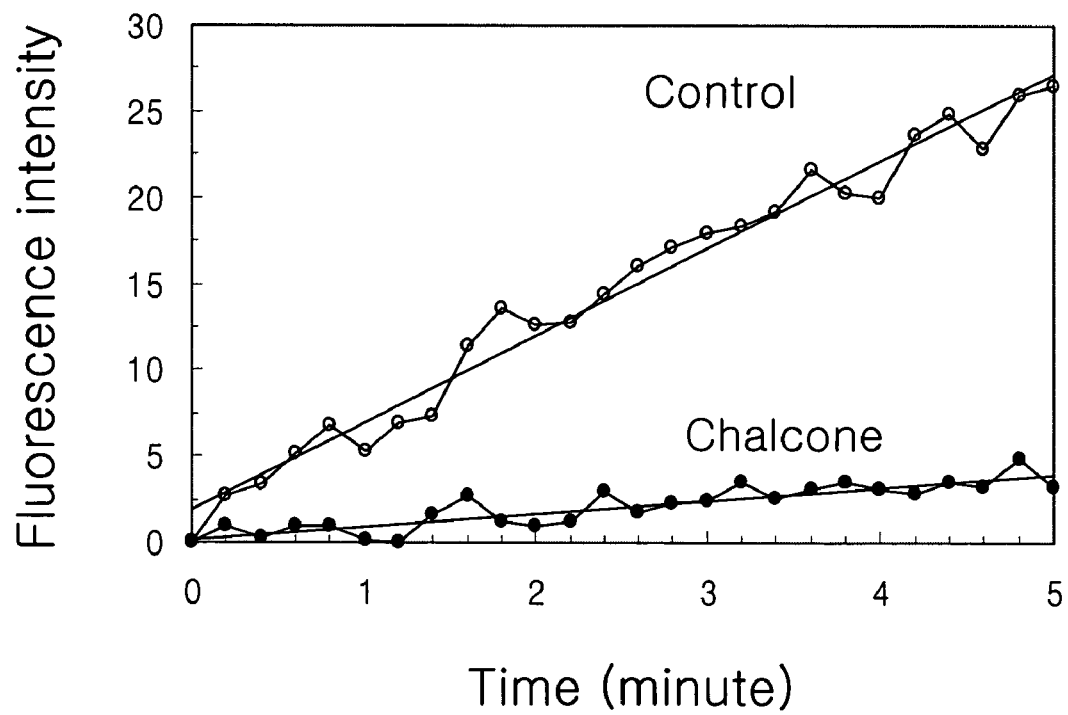
FIG. 2 is a graph showing the inhibition of MMP-9 by chalcone.

FIGS. 1 and 2 are diagrams of activity of MMP-1 and MMP-9. As shown in figures, about 75% of MMP-1 and 76% of MMP-9 activity were inhibited by chalcone. Chalcone also inhibits activity of MMP-2 and MMP-13 by about 80%. The extent of MMP inhibition by each derivative was similar to or greater than that by parent compound, chalcone. The results for MMP-2 and MMP-13 inhibition are summarized in Table 1.

TABLE 1

MMP Inhibitory activity of chalcone or its derivatives

| Compound (50 µM) | MMP-2 inhibition (% inhibition) | MMP-13 inhibition (% inhibition) |
| --- | --- | --- |
| Control (DMSO) | 0 | 0 |
| Chalcone (Indofine Chemical Co.) | 79.9 | 80.0 |
| Phloretin (Sigma Chemical Co.) | 87.2 | 77.0 |
| 4-methoxy chalcone ($R_3 = CH_3O$) | 92.7 | 83.9 |
| 2-hydroxy chalcone ($R_1 = OH$) | 90.4 | 89.9 |
| 4-hydroxy chalcone ($R_3 = OH$) | 95.9 | 94.5 |
| 4'-methoxy chalcone ($R_8 = CH_3O$) | 99.1 | 86.8 |
| 2',4'-dimethoxy chalcone ($R_6 = CH_3O$, $R_8 = CH_3O$) | 92.5 | 83.4 |

Experimental Example 2

Effect of Chalcone or its Derivatives on Tube Formation of HUVEC

The effect of chalcone or its derivatives on human endothelial cells was investigated to evaluate the biological effect of chalcones as MMP inhibitors. Since MMPs are responsible for the degradation of extracellular matrix, chalcone or its derivatives can inhibit the formation of tubular network of vessel, which represent migration and differentiation of endothelial cell.

Blood vessel endothelial cells, human umbilical vein endothelial cells (HUVECs), were isolated from freshly obtained cords after cesarean section according to Grants' method (Grants D. S., et al., *Cell*, 58, pp933-943, 1989). They were identified by immunocytochemical staining with anti-Factor VIII antibody. HUVECs cultured on Matrigel (BD Bioscience, Bedford, Mass., USA) were treated with 50 µM of chalcone or its derivatives, and further incubated at 37° C. for 8-16 hrs. As a control, the procedure was repeated with the solvent of the above compounds.

Figure 3:
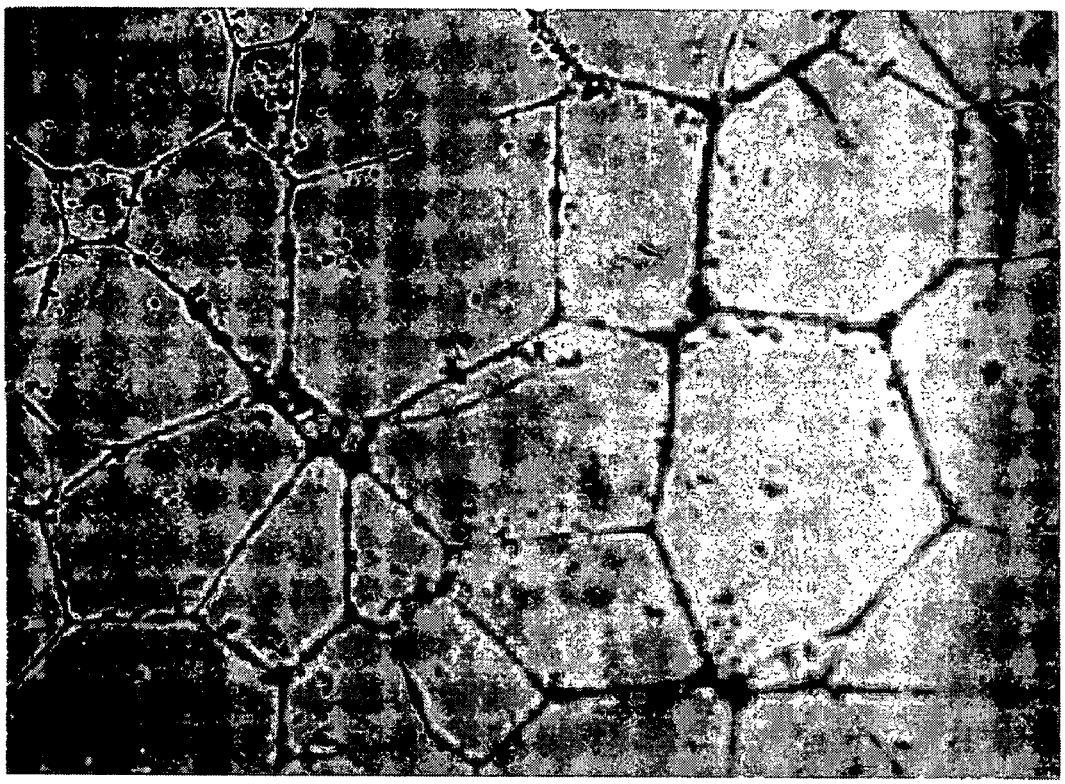
FIG. 3 is a picture showing tube formation of HUVEC treated with 0.5% DMSO.
Figure 4:
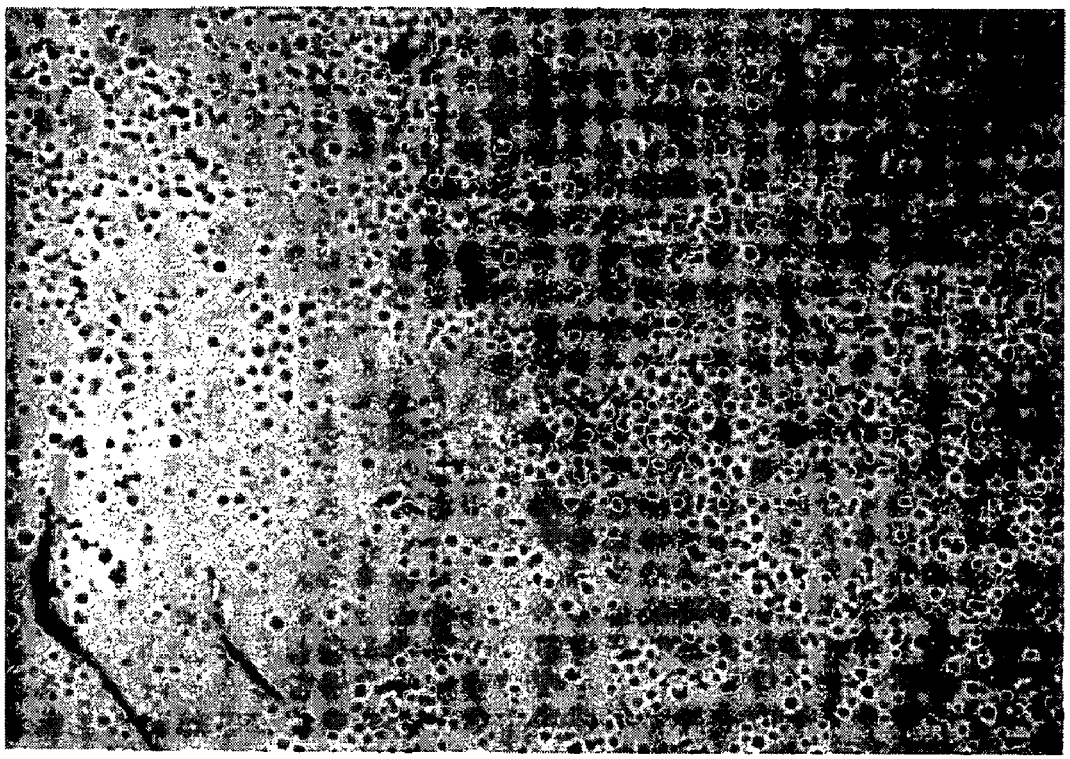
FIG. 4 is a picture showing tube formation of HUVEC treated with chalcone.
Figure 5:
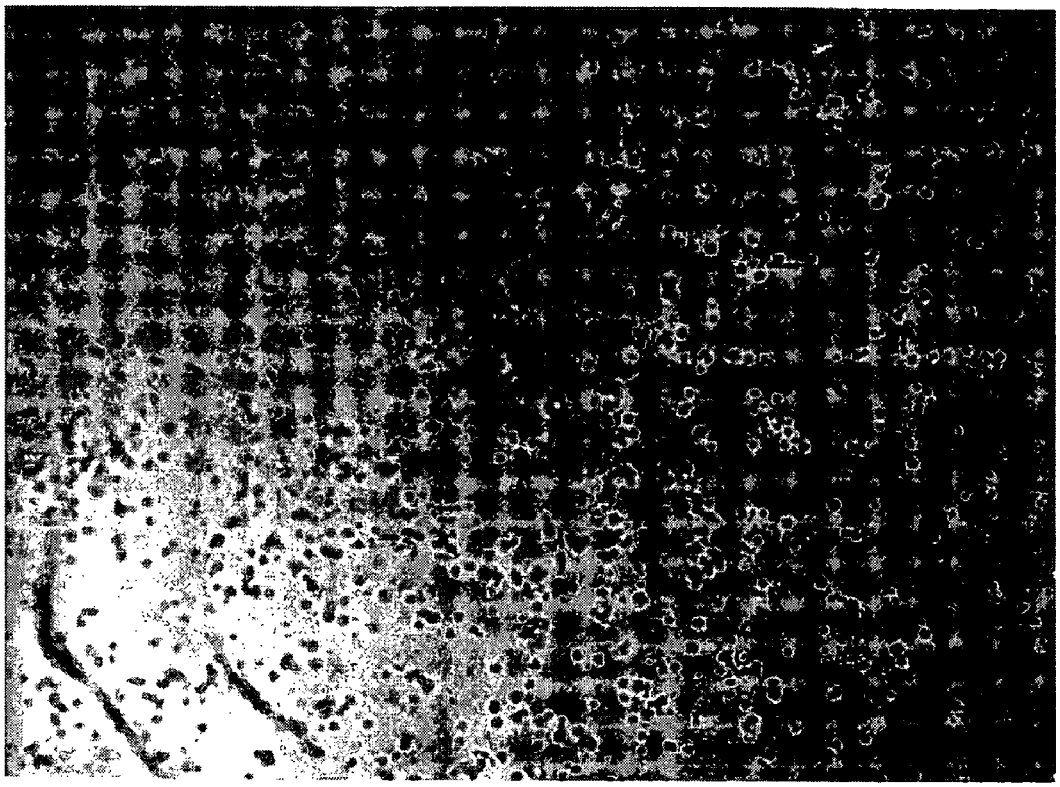
FIG. 5 is a picture showing tube formation of HUVEC treated with 4'-methoxychalcone.

FIG. 3 shows that a tubular network is formed as a process of neovascularization, when they are grown on Matrigel. However, the microvascular network was disconnected when HUVECs grown on Matrigel were treated with 50 µM of chalcone (FIG. 4) or 4'-methoxy chalcone (FIG. 5). These data show that chalcone and its derivatives can inhibit angiogenesis by inhibiting MMP activity.

Experimental Example 3

Effect of Chalcone or its Derivatives on Angiogenesis by Rat Aortic Ring Assay

The effect of chalcone or its derivatives on angiogenesis was studied by culturing aortic explants in three-dimensional matrix gels according to the procedure of Kruger and Figg (Clinical Cancer Research 7:1867-1872, 2001).

Thoracic aortas were excised from 8-week-old male Sprague Dawley rats and the fibroadipose tissue was removed. The aortas were sectioned into 1-mm-long cross-sections, rinsed with Human Endothelial-SFM (GIBCO), placed on the Matrigel-coated wells, covered with additional 50 ul Matrigel, and allowed to gel for more than 30 min at 37° C., 5% $CO_2$. All the rings were cultured in Human Endothelial-SFM (GIBCO) supplemented with 200 ug/ml of ECGS (Endothelial Cell Growth Supplement, Sigma) as an angiogenesis inducer. Chalcone diluted with ethanol was added to the culture medium at final concentrations of 1 uM and 100 uM. 1% of ethanol only was added to the culture medium as a vehicle control.

All assays were performed by using 5 aortic rings per sample. Aortic rings were photographed on day 10. The area of angiogenic sprouting was calculated using Image-Pro Plus software program (Media Cybernetics). Microvessel densities are reported in percent area. 1 uM of chalcone (18.5±1.2) inhibited microvessel formation by 5.1% while 100 uM of chalcone (1.7±0.1) inhibited microvessel formation by 91.3% compared to control (19.5±1.8) in rat aortic ring assay.

Experimental Example 4

Anti-Inflammation Activity of Chalcone or its Derivatives by Ear Edema Model

Figure 6:
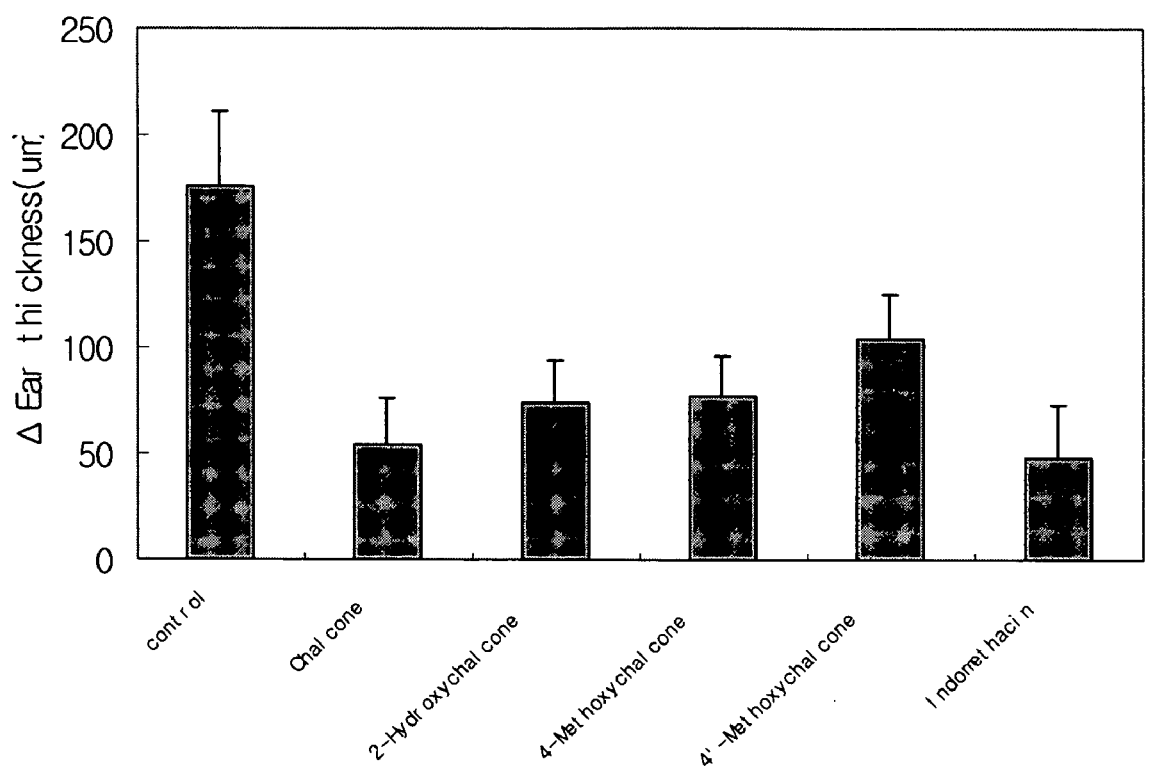
FIG. 6 is a graph showing the effects of chalcone or its derivatives on TPA-induced mouse ear edema.
Figure 7:
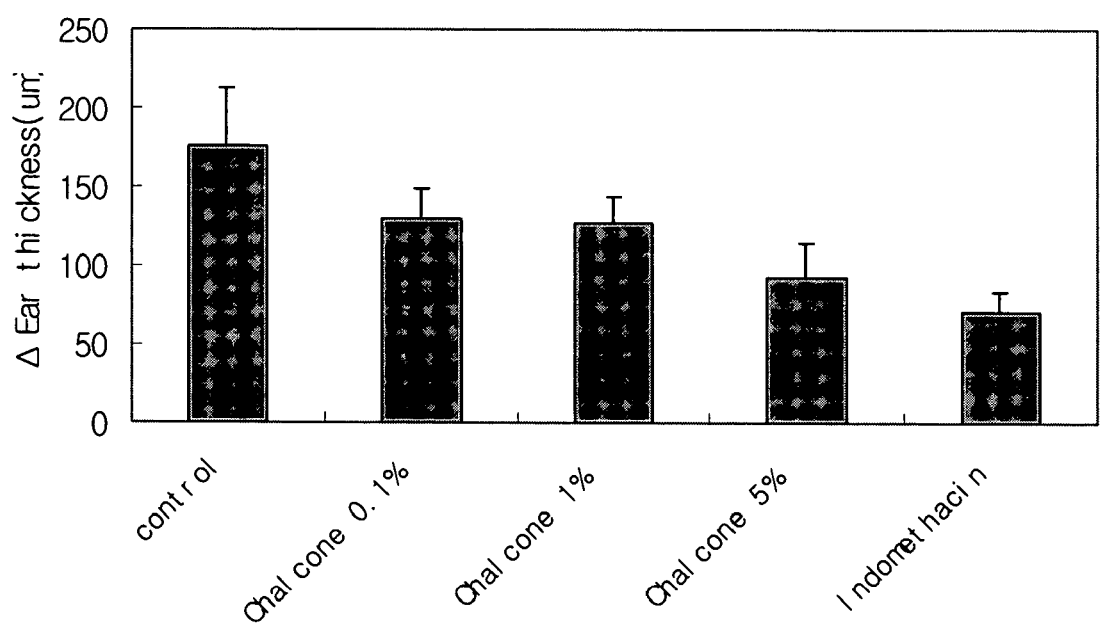
FIG. 7 is a graph showing the effect of dose with chalcone on inhibition of TPA-induced ear edema.

To observe the anti-inflammatory effects of chalcone or its derivatives edema was induced in the ear by topical application of 10 ul of TPA (Tetradecanoylphorbol acetate) in acetone (2.5 ug/ear) to both the inner and outer surface of one ear of each 6-week-old ICR mouse. 5% of Chalcone or its derivatives diluted with acetone were applied separately to each ear topically immediately after TPA. The reference drug, indomethacin (0.5 mg/ear), was administered as a positive control. Ear thickness was measured before and 4 hours after treatment with the irritant using a micrometer (Mitutoyo Co.). Ear thickness was expressed as the mean of the difference between thickness before and after challenge. Inhibition ratio percentage of edema was expressed as the reduction in thickness with respect to the control treated only with TPA. As shown in FIG. 6 and Table 2, chalcone or its derivatives suppressed the TPA-induced ear edema. Chalcone or its derivatives reduced it by more than 40% although to a lesser extent than did indomethacin (0.5 mg/ear) and chalcone showed the greatest potency. The anti-inflammatory activity of chalcone was shown to be dose dependent (FIG. 7).

TABLE 2

Anti-inflammatory effect of Chalcone or its
derivatives on TPA-induced ear edema

| Group | Δ Ear thickness (um ± S.D) | Inhibition ratio (%) |
| --- | --- | --- |
| Control (TPA) | 176 ± 35 | 0 |
| Chalcone | 54 ± 22 | 69.3 |
| 2-Hydroxychalcone | 74 ± 20 | 58.0 |
| 4-Methoxychalcone | 77 ± 19 | 56.2 |
| 4'-Methoxychalcone | 104 ± 21 | 40.9 |
| Indomethacin | 48 ± 25 | 72.7 |

Experimental Example 5

Effect of Chalcone on Comedolysis by EIC (Experimentally Induced Comedones) Formation Effects of chalcone on comedolysis were studied using subjects of ten mature New Zealand white rabbits, which were bred to approximately 2 kg of body weight for several weeks. In order to generate EIC, 50% oleic acid in polyethylene glycol was applied to both ears of rabbits for 2 weeks. The experimental agent was applied to the ventral surface near the auditory canal once a day with the tip of a cotton stick. 18 ears of rabbits were divided into three groups, and only one of ethanol-propylene glycol (1:1) (control), 1% chalcone in ethanol-propylene glycol (1:1), or 5% chalcone in ethanol-propylene glycol (1:1) was applied on each groups for 3 weeks. The remaining 2 ears were left untreated. Biopsy specimens were taken at 3 week by punch and specimens were fixed in 10% formalin solution and embedded in paraffin for light microscopic examination. Sections of 5 μm thickness were cut and hematoxylin and eosin stain were performed. Under light microscope, fairly large comedones were formed showing hyperplasia and hyperkeratosis of epithelium in specimen treated with vehicle only. The formation of comedones decreased in specimen treated with 1% or 5% of chalcone.

Experimental Example 6

Effect of Chalcone on Skin Photoaging

Effects of chalcone on skin photoaging were studied using mouse skin wrinkle induced by UV irradiation. 6-week male albino hairless HOS:HR1 mice were used for wrinkle formation induced by long-term repeated UVB irradiation. Wrinkles were formed according to the modified method described by Bissett et al (Photochem Photobiol 46: 367-378, 1987) The dose was set at 60 mJ per $cm^2$ for 4 weeks and increased to 120 mJ per $cm^2$ for 11 weeks. The frequency of irradiation was set at three times per week. In this protocol, wrinkles began to be observed macroscopically in the dorsal region from about 8 week after initiation of irradiation, and deep wrinkles were formed at 12 week. 30 hairless mice were divided into three groups, and only one of ethanol-propylene glycol (7:3) (control), 1% chalcone in ethanol-propylene glycol (7:3), or 5% chalcone in ethanol-propylene glycol (7:3) was applied on each groups for 15 weeks. 100 μl of the experimental agent was applied to the dorsal region three times weekly just after UVB exposure. At 15 week after initiation of repeated UVB irradiation, each hairless mouse was anesthetized, and the degree of wrinkle formation was evaluated according to Table 3. The UVB-induced wrinkle formation was significantly inhibited by the topical application of 1% or 5% of chalcone as compared with that in the vehicle-treated group at 15 week after initiation of UVB irradiation.

TABLE 3

Criteria for grading of mouse skin wrinkles.

| Grade | Observation |
| --- | --- |
| 0 | No wrinkles |
| 2 | A few shallow wrinkles across the back skin are observed occasionally. |
| 4 | Shallow wrinkles across the back skin are observed on the whole surface. |
| 6 | Some deep, long wrinkles across the back skin are observed. |
| 8 | Deep, long wrinkles across the back skin are observed on the whole surface. |

Experimental Example 7

Effect of Chalcone on Skin Sensitization by Human Patch Test

The effect of chalcone on skin sensitization was studied by general method of skin patch test. The skin patch test was done against human subjects of ten adults. Test patch (2 cm×2 cm) included 0.2 ml of cream containing 0.01%-1.0% chalcone. The patches were applied to the backs of subjects. The patch was removed after 48 hours or 96 hours, and the skin responses of subjects were recorded and evaluated as shown in Table 4. The skin average reactivity calculated by equation 1 was interpreted as the degree of skin sensitivity in Table 5. According to the skin patch test, chalcone was nonreactive to skin sensitization (Table 6).

TABLE 4

Criteria on the evaluation of skin responses.

| grade | | results |
| --- | --- | --- |
| +/− | 0.5 | doubtful reaction |
| + | 1.0 | weak(nonvesicular) reaction-erythema and/or papules |
| ++ | 2.0 | strong(edematous or vesicular) reaction-erythema, papule and/or small vesicles |
| +++ | 3.0 | extreme reaction all for the foregoing plus large vesicles, bullae, and at times, ulceration |

$$\text{Skin average reactivity} = \frac{\text{Grade} \times \text{No. of responses} \times 100 \times 1/2}{(\text{Maximum grade}) \times (\text{No. of Total Subjects})} \quad \text{Equation 1}$$

TABLE 5

The degree of skin sensitivity

| Skin average reactivity | interpretation |
| --- | --- |
| 0.0-0.9 | nonreactive |
| 1.0-2.9 | mild |
| 3.0-4.9 | moderate |
| >5.0 | severe |

TABLE 6

| | | The result of skin patch test | | | | | | | | | | |
|---|---|---|---|---|---|---|---|---|---|---|---|---|
| | | 48 hrs | | | | 96 hrs | | | | Reaction grade(%) | | |
| No. | Sample | ± | + | 2+ | 3+ | ± | + | 2+ | 3+ | 48 hrs | 96 hrs | Mean Result |
| 1 | 0.01% Chalcone cream | 0 | 0 | 0 | 0 | 0 | 0 | 0 | 0 | 0.00 | 0.00 | 0.00 nonreactive |
| 2 | 0.1% Chalcone cream | 0 | 0 | 0 | 0 | 0 | 0 | 0 | 0 | 0.00 | 0.00 | 0.00 nonreactive |
| 3 | 1.0% Chalcone cream | 1 | 0 | 0 | 0 | 0 | 0 | 0 | 0 | 0.28 | 0.00 | 0.14 nonreactive |

Experimental Example 8

Making a Salt of the Inventive Compound

To a stirred solution of the inventive compound (5 mmol) in 10 mL $CH_2Cl_2$ (dichloromethane) is added dropwise, a solution of sodium ethylhexanoate (5.2 mmol) in 30 mL $CH_2Cl_2$. After stirring at room temperature for 1 h, the precipitate is filtered and the filter cake is washed with $CH_2Cl_2$ to give a salt of the compound.

All of the references cited herein are incorporated by reference in their entirety.

Those skilled in the art will recognize, or be able to ascertain using no more than routine experimentation, many equivalents to the specific embodiments of the invention specifically described herein. Such equivalents are intended to be encompassed in the scope of the claims.

What is claimed is:

1. A method of reducing wrinkles in a subject with aging skin, said method comprising
    administering to the subject a therapeutically effective amount of a composition comprising a compound selected from 4-methoxychalcone, 4'-methoxychalcone or 2', 4'-dimethoxychalcone.

2. The method according to claim 1, wherein the compound is 4'-methoxychalcone.

3. The method according to claim 1, wherein the skin aging is photoaging.

4. The method according to claim 1, wherein the composition is administered topically.

5. The method according to claim 1, wherein the composition is a paste.

6. The method according to claim 1, wherein the composition is a solution.

7. The method according to claim 1, wherein the composition is a cream.

8. The method according to claim 1, wherein the composition is a lotion.

9. The method according to claim 1, wherein the composition is a gel.

10. The method according to claim 1, wherein the composition is a balm.

11. The method according to claim 1, wherein the composition is a patch.

12. The method according to claim 1, wherein the composition is a spray.

13. The method according to claim 1, wherein the composition is an ointment.

* * * * *